United States Patent
Holman et al.

(10) Patent No.: US 6,225,469 B1
(45) Date of Patent: May 1, 2001

(54) PROCESS FOR THE PREPARATION OF 7-ALKOXYALKYL-1,2,4-TRIAZOLO[1,5-A] PYRIMIDINE DERIVATIVES

(75) Inventors: Nicholas John Holman, Nottingham (GB); Stefan Koser, Ludwigshafen (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/242,465
(22) PCT Filed: Aug. 13, 1997
(86) PCT No.: PCT/EP97/04433
§ 371 Date: Feb. 17, 1999
§ 102(e) Date: Feb. 17, 1999
(87) PCT Pub. No.: WO98/07724
PCT Pub. Date: Feb. 26, 1998

(30) Foreign Application Priority Data

Aug. 23, 1996 (DE) .................................................. 9617727

(51) Int. Cl.$^7$ ................................................ C07D 487/04
(52) U.S. Cl. .............................................................. 544/256
(58) Field of Search ............................................. 544/256

(56) References Cited

U.S. PATENT DOCUMENTS

| 4,080,325 | 3/1978 | Ellard ................................... 544/260 |
| 4,421,913 | 12/1983 | Ellard et al. ........................ 544/260 |
| 5,177,206 | 1/1993 | Johnson et al. ..................... 544/263 |

FOREIGN PATENT DOCUMENTS

95/10521   4/1995   (WO) .

OTHER PUBLICATIONS

Lincoln et al., Aust. J. Chem., 34, 1981, 283–289.
Camp et al., Aust. J. Chem., 41, 1988, 1835–1839.
von Itzstein, Synt. Comm., 20(13), 1990, 2049–2057.
Kang et al., Tetrahedron Letters. 37(52), 1996, 9317–9320.

Primary Examiner—Richard L. Raymond
Assistant Examiner—Venkataraman Balasubramanian
(74) Attorney, Agent, or Firm—Keil & Weinkauf

(57) ABSTRACT

An improved process for the preparation of 1,2,4-triazolo[1,5-a]pyrimidine compounds comprising the reaction involving a compound of formula II

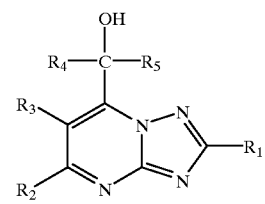

and a compound of formula III

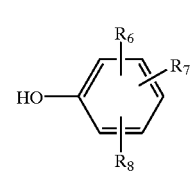

in the presence of an oxidizing agent and a reducing agent, wherein a metal salt is added to form a complex with the oxidized reducing agent produced in the process, and this complex is separated from the desired product.

18 Claims, No Drawings

PROCESS FOR THE PREPARATION OF 7-ALKOXYALKYL-1,2,4-TRIAZOLO[1,5-A] PYRIMIDINE DERIVATIVES

The present invention relates to an improved process for the preparation of certain 1,2,4-triazolo[1,5a]pyrimidines which are useful in the treatment and/or prophylaxis of seizures, neurological disorders such as epilepsy and/or conditions in which there is neurological damage such as stroke, brain trauma, head injuries and haemorrhage.

Compounds of Formula A

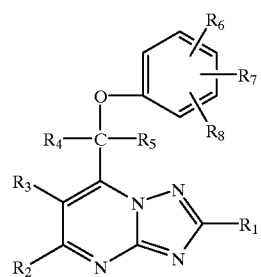

A in which R, represents H or optionally substituted alkyl, alkoxy or alkanoyl; $R_2$ and $R_3$ independently represent H or optionally substituted alkyl, alkoxy, alkanoyl, alkylthio, alkylsulphinyl or sulphonyl; $R_4$ and $R_5$ independently represent H, alkyl or together with the carbon atom to which they are attached represent optionally substituted cycloalkylidene; and $R_6$, $R_7$ and $R_8$ independently represent H, halo hydroxy, mercapto, cyano or optionally substituted alkyl, alkanoyl, alkoxy, alkoxycarbonyl, carboxy, alkanoyloxy, alkylthio, alkylsulphinyl, alkylsulphonyl, alkylsulphonylamino, sulphamoyl, carbamoyl, alkylcarbanoyl or alkanoylamino; processes for their preparation, and their use in the treatment and/or prophylaxis of seizures, neurological disorders such as epilepsy and/or conditions in which there is neurological damage such as stroke, brain trauma, head injuries and haemorrmage are described in WO95/10521 (Knoll AG).

In WO95/10521, there is a disclosure of the preparation of compounds of formula A by coupling alcohols of formula B

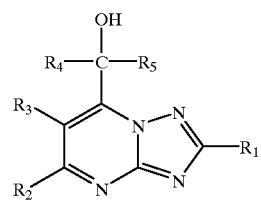

B with phenols of formula C

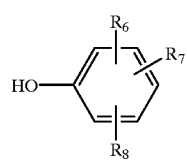

C in the presence of a redox coupling agent which, for example, in the "Mitsunobu" reaction is diethyl azodicarboxylate with triphenylphosphine. This reaction leads to the production of triphenylphosphine oxide which is separated from the compound of formula A by flash column chromatography on silica gel.

The "Mitsunobu" reaction using a redox couple, in which the reducing agent is triphenylphosphine, is a very good method for producing chiral compounds of formula A because it results in generally good yields with high stereoselectivity (inversion) and is relatively simple to carry out since the alcohol activation and displacement reactions take place in a single transformation—usually at room temperature. However, the resultant formation of triphenylphosphine oxide is a disadvantage because it is difficult to remove from the desired product. Flash column chromatography is an acceptable laboratory-scale solution to this problem, but is not practicable on an industrial scale in terms of cost, time efficiency and ease of handling.

One solution to the problem is to use for example a basic phosphine, such as diphenyl(2-pyridyl)phosphine or (4dimethylamirophenyl)diphenylphosphine, as the reducing agent in the redox couple. This facilitates product isolation since the resulting phosphine oxide is removed by aqueous acid washing. However, these basic phosphines may not be suitable for chiral compounds of formula A since the acid washing may cause racemisation of the chiral centre, and some compounds of formula A are soluble in strong acid so that separation from the phosphine oxide would not be achieved by acid washing. Furthermore, use of these basic phosphines is not commercially viable on a production scale. In addition, the yield can be substantially reduced by using a reducing agent other than triphenylphosphine. Polymer-bound phosphines may also be used to avoid the formation of triphenylphosphine oxide. However, these phosphines are expensive and the reaction is significantly slower so that time and cost efficiency are compromised.

Surprisingly, we have now found a means of reducing the level of triphenylphosphine oxide from the desired compound of formula A which is inexpensive, quick, requires mild conditions and neutral pH, and is very easy to carry out both on a laboratory scale and on a production scale. This new process enables the use of triphenylphosphine in the redox couple (thus resulting in good stereospecificity and yield) and the efficient removal of the unwanted triphenylphosphine oxide. The process can also be applied to other tri-substituted phosphine redox couples if desired, since it is effective at reducing the levels of other phosphine oxides. Other elements of group V of the periodic table, such as arsenic and antimony, are also able to form tri-substituted compounds (arsines and stibines) which may be used as reducing agents. The process of the present invention may also be applied to reducing the level of the oxides of such compounds.

It will be understood that for the remainder of this document, the term "tri-substituted phosphine, arsine and/or stibine" refers to tri-substituted phosphine, arsine and/or stibine in which the substituents are organic moieties.

The present invention comprises a process for the preparation of compounds of formula I

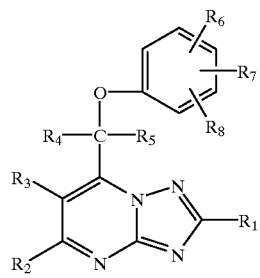

including pharmaceutically acceptable salts, solvates, racemates, enantiomers, diastereoisomers and mixtures thereof in which:

$R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $C_{1-6}$alkyl or $R_4$ and $R_5$ combined together with the carbon atom to which they are attached represent $C_{3-6}$cycloalkylidene (each alkyl or cydoalkylidene being optionally substituted with one or more of halo, cyano, hydroxy, amino or $C_{1-6}$-alkyl); and $R_6$, $R_7$ and $R_8$ independently represent H, halo, hydroxy, mercapto, nitro, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-7}$alkoxy, $C_{2-6}$alkoxycarbonyl, carboxy, $C_{1-6}$alkanoyloxy, $C_{1-6}$alkyfthio, $C_{1-6}$alkylsulphinyl, $C_{1-6}$alkylsulphonyl, $C_{1-6}$alkyl-sulphonylamino, sulphamoyl, carbamoyl, $C_{2-6}$ikylcarbamoyl or $C_{1-6}$alkanoylamino; said process comprising the reaction involving an alcohol of formula II

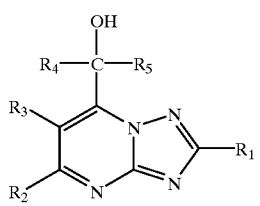

in which $R_1$, $R_2$, $R_3$, $R_4$ and $R_5$ are as defined above, with a phenol of formula III

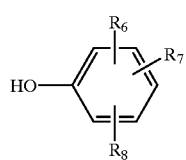

in which $R_6$, $R_7$ and $R_8$ are as defined above, in the presence of an inert diluent and at least one redox couple comprising an oxidising agent and a reducing agent which is selected from a tri-substituted phosphine, arsine or stibine wherein the reducing agent becomes oxidised; wherein a) a metal salt is added to form a complex or complexes with the oxidised reducing agent or agents produced in the process, and b) the resultant complex or complexes is/are separated from the desired product.

It will be understood that the oxidising agent becomes reduced during the process, and that the reduced oxidising agent may be removed from the desired product either before or after steps a) and b) are carried out. Preferably, the reduced oxidising agent is removed from the desired product after steps a) and b) are carried out.

It will be understood that any group mentioned herein which contains a chain of three or more atoms signifies a group in which the chain may be straight or branched. For example, an alkyl group may comprise propyl which includes n-propyl and isopropyl and butyl which includes n-butyl, sec-butyl, isobutyl and tert-butyl. The total number of carbon atoms is specified herein for certain substituents, for example $C_{1-6}$alkyl signifies an alkyl group having from 1 to 6 carbon atoms. The term 'halo' as used herein signifies fluoro, chloro, bromo and iodo. The term 'halide' as used herein signifies fluoride, chloride, bromide or iodide. The term 'optionally substituted' as used herein, unless immediately followed by a list of one or more substituent group or groups, means optionally substituted with one or more of halo, cyano, hydroxy, amino or $C_{1-6}$alkyl. When the phenyl ring substituents $R_6$, $R_7$ and $R_8$ are other than H, the substituent may replace any H attached to a carbon atom in the ring and may be located at any such position of the ring, ie up to three of positions 2, 3, 4, 5 or 6.

Certain compounds of formula I may form salts with organic or inorganic acids and or bases. As stated above, reference herein to compounds of formula I includes all salts of compounds of formula I which are pharmaceutically acceptable.

The term "inert diluent" means a diluent commonly used by those skilled in the art which is inert to the reaction conditions. Preferably the inert diluent is a solvent or mixture of solvents selected from tetrahydrofuran, diethyl ether, 1,4dioxane, toluene, acetonitrile, dichloromethane, dimethylfornamide, diisopropyl ether, t-butyl methyl ether, and ethyl acetate.

The separation of the resultant complex or complexes from the desired product [step b) of the present invention] may be achieved by one of the following methods. In cases where the complex precipitates out of the solution, the separation may be achieved by filtration, decantation, or centrifugation. Preferably, separation is achieved by filtration. It will be understood that the desired product may then be obtained from the filtrate for example by evaporation or crystallisation. Alternatively, if the complex is soluble in the inert diluent, and therefore does not precipitate out of the solution, the inert diluent may be removed by evaporation and replaced by a solvent, in which the complex and the desired product have different solubilities. Suitably the solvent is selected from water, methanol, ethanol and/or propan-2-ol and/or any of the inert diluents listed previously herein, or it may be a mixture of any of these. When the desired product is more soluble than the complex, for example when the solvent is toluene, the insoluble complex can be separated and the desired product obtained as described above. Alternatively, when the complex is more soluble than the desired product, for example when the solvent is propan-2-ol, the insoluble desired product can then be separated by filtration, decantation, or centrifugation.

Optionally, further purification of the desired product may be carried out after steps a) and b). Further purification may comprise, for example trituration with a suitable solvent, for example a $C_{1-4}$ alcohol or mixture thereof, preferably a propanol, most preferably propan-2-, and/or crystallisation from such a suitable solvent. Preferably, the further purification comprises trituration with propan-2-ol or crystallisation from propan-2-ol.

It will be appreciated by those skilled in the art that steps a) and b) of the process may be carried out iteratively if desired. Preferably, steps a) and b) of the process are carried out until the level of tri-substituted phosphine, arsine and/or stibine oxide has been reduced sufficiently to enable the desired product to be isolated by the further purification described above, in a form which is substantially free of tri-substituted phosphine, arsine and/or stibine oxide. Preferably, the level of tri-substituted phosphine, arsine and/or stibine oxide is reduced to 15% of the product mixture or less. Most preferably, the level of tri-substituted phosphine, arsine and/or stibine oxide is reduced to substantially 0% (wherein no triphenylphosphine oxide is detectable by Gc or HPLC analysis).

The metal salt of step a) may be added during or after the reaction involving the compounds of formulae II and III, subsequent to an inert diluent change after completion of the reaction involving the compounds of formulae II and III, or after removal of the reduced oxidising agent. Preferably, the metal salt is added after the reaction involving the compounds of formulae II and III.

It will be appreciated that the phrase "a metal salt is added" in step a) is intended to include the addition of a metal salt and/or the addition of reactants suitable for the formation of a metal salt in situ, for example a metal and an acid, or a metal oxide and an acid. The present invention therefore includes both the above additions.

Preferably the metal salt is added in a quantity ranging from 0.25 to 5 molar equivalents of the reducing agent, more preferably in a quantity ranging from 1.5 to 3 molar equivalents of the reducing agent Preferably, the compounds of formula II and III, and the oxidising agent and the reducing agent are present in about equimolar quantities.

Preferably the reaction involving compounds of formula 11 and III is carried out at a temperature in the range –20 to 100° C., more preferably in the range –10 to 40° C.

Preferably, when step a) is carried out after the reaction involving the compounds of formula II and III, the mixture is brought to a temperature in the range 0 to 120° C., preferably at 20 to 120° C., most preferably the mixture is heated under reflux at the boiling point temperature of the inert diluent, for up to 16 hours, preferably for up to 6 hours, more preferably for 1 to 4 hours, subsequent to the addition of the metal salt, then the mixture is cooled to a temperature in the range –100° C. to ambient temperature.

The metal salt may be a halide (for example fluoride, chloride, bromide or iodide), sulphate, nitrate, perchlorate, bicarbonate, carbonate, acetate, citrate or benzoate salt of an alkali, alkaline earth, group IIb, transition or lanthanide metal, or a solvate thereof, for example a hydrate or organic solvate. Preferably the metal is selected from lithium, sodium, potassium, magnesium, calcium, barium, strontium, samarium (III), zinc, iron (II), iron (III), manganese (II), cobalt (II), cobalt (III), nickel, copper (I) and copper (II). Preferably, the metal salt is a halide salt of magnesium, copper (I), manganese (II), iron (III), samarium (III) or zinc. More preferably the salt is the chloride salt or iodide salt, most preferably the chloride salt. Preferably the metal salt is magnesium chloride, copper (I) chloride, or zinc chloride. It is desirable that the metal salt is low in cost, toxicity, Lewis acidity and oxidising ability. Especially preferred is magnesium chloride.

The salt may be added to the mixture in the form of powder, pellets, or a solution or slurry in an inert diluent In one preferred form magnesium chloride is added as a powder.

The redox couple may be any of those known in the art as suitable for this type of reaction. Preferably the reducing agent is a phosphine. For example, the reducing agent may be selected from tris($C_{1-4}$akyl)phosphine, triphenylphosphine, tris(3-chlorophenyl)phosphine, tris(4-chlorophenyl)phosphine, tris(3-methylphenyl)-phosphine, tris(4-methylphenyl)phosphine, tris(3-methoxyphenyl)phosphine, tris(4-methoxyphenyl)phosphine, phenoxydiphenylphosphine and diphenoxyphenylphosphine. Preferably, the oxidising agent is selected from di($C_{1-5}$alkyl) azodicarboxylate, di($C_{1-5}$alkyl) azodicarboxamide (N-substituted by $R_1$ and $R_2$ which may independently represent H or a straight or branched $C_{1-8}$alkyl or cyclic $C_{3-8}$alkyl group or $R_1$ and $R_2$ together represent a $C_{4-6}$alkylene chain), polymer (such as polystyrene) supported methyl azodicarboxylate (as described in JACS, 111, p3973-3976, 1989), 4methyl-1,2,4triazolidine-3,5-dione, dibenzoylperoxide, dimethyl ketomalonate and 3methylbenzothiazole-2-selone. Preferably, the redox couple is triphenylphosphine with diisopropyl azodicarboxylate or diethyl azodicarboxylate.

Therefore, the present invention provides a process for the preparation of 7-[1-(4-chlorophenoxy)ethyl]-1,2,4triazolo[1,5-a]pyrimidine including the racemate, enantiomers and mixtures thereof, said process comprising the reaction involving the compound of formula II which is 1-(1,2,4triazolol[1,5-a]pyrimidin-7-yl)ethanol, including the racemate, enantiomers and mixtures thereof, and the compound of formula III which is 4chlorophenol in the presence of an inert diluent and at least one redox couple comprising an oxidising agent, which is diisopropyl azodicarboxylate or diethyl azodicarboxylate, and a reducing agent, which is triphenylphosphine, wherein the reducing agent becomes oxidised; wherein a) a halide salt of magnesium, copper (I), iron (III), samarium (III) or zinc is added after the reaction involving the compounds of formulae II and III to form a complex or complexes with the oxidised reducing agent or agents produced in the process, and b) the resultant complex or complexes is/are separated from the desired product by filtration, and optionally further purification of the desired product is carried out by trituration with propan-2-ol and/or crystallisation from propan-2-ol.

Preferably, the compound of formula II is 1-(1,2,4-triazolo[1,5-a]pyrimidin-7-yl)ethanol, most preferably it is (S)-1-(1,2,4-triazolo[1,5-a]pyrimidin-7-yl)ethanol.

Preferably, the compound of formula III is 4-chlorophenol.

Preferably, the compound of formula I is 7-[1-(4-chlorophenoxy)ethylo-1,2,4-triazolo[1,5-a]pyrimidine, most preferably it is (R-7-[1-(4-chlorophenoxy)ethyl]-1,2,4-triazolo[1,5-a]pyrimidine.

Suitably, the process reduces the level of tri-substituted phosphine, arsine and/or stibine oxide by at least 20%. Preferably the level of tri-substituted phosphine, arsine and/or stibine oxide is reduced by at least 30%. More preferably the level of tri-substituted phosphine, arsine and/or stibine oxide is reduced by at least 50%. Especially preferably, the level of tri-substituted phosphine, arsine and/or stibine oxide is reduced by at least 70%. Most preferably the level of tri-substituted phosphine, arsine and/or stibine oxide is reduced by at least 85%. The percentage reduction is calculated by comparing the % of oxide present, by normalisation by gas-liquid chromatography, in the product mixture before and after the process of the present invention is carried out.

The invention will now be illustrated by the following non-limiting examples. The examples are illustrative only, and have not necessarily been carried out under optimal conditions. The final product of each example was characterised using one or more of the following techniques: elemental analysis; infra-red spectroscopy; nuclear magnetic resonance spectroscopy (nmr); gas-liquid chromatography (Gc); and high performance liquid chromatography (HPLC). Temperatures are given in degrees Celsius. Under Gc analysis, triphenylphosphine oxide and the complexes comprising triphenylphosphine oxide may have the same retention time so that figures for percentage triphenylphosphine oxide levels after complexation may refer to total triphenylphosphine oxide levels (both free and complexed).

EXAMPLE 1

A solution of diisopropyl azodicarboxylate (27.2 g, 1.1 eq) in dry tetrahydrofuran (40 ml) was added over 45 minutes to a stirred mixture of 1-(1,2,4-triazolo[1,5-a]pyrimidin-7-yl)ethanol (20 g), 4-chlorophenol (17.2 g, 1.1 eq), triphenylphosphine (35.2 g, 1.1 eq) and tetrahydrofuran (240 ml) under nitrogen at 0–50° C. and then stirred overnight at ambient temperature. Water (4 ml, 1.85 eq) was added and the mixture heated under reflux for 30 minutes. Magnesium chloride (28 g, 2.5 eq) was added and the stirred mixture heated under reflux for 2.5 hours, cooled to 0° C. and filtered, washing the filter pad with tetrahydrofuran (2×50 ml). The solvent was removed in vacuo and the residual oil triturated with ethyl acetate (300 ml) then diluted with t-butyl methyl ether (100 ml. The mixture was filtered and the filter pad washed with a 3:1 mixture of ethyl acetate and t-butyl methyl ether (2×50 ml). The filtrate was washed with water (2×100 ml), sodium hydroxide (0.5 M, 2×50 ml), brine (50 ml), and dried ($MgSO_4$). The solvent was removed in vacuo to give a residue. This was triturated with propan-2-ol (40 ml), left to stand overnight at <50 C., then filtered to give a solid (27 g).

Propan-2-ol (50 ml) was added to the solid and the mixture allowed to stand at 0° C. overnight. The mixture was filtered and the solid washed with cold (0° C.) propan-2-ol (2×10 ml) to give 7-[1-(4-chlorophenoxy)ethyl 1,2,4-triazolol[1,5-a]pyrimidine (26 g) which was analysed for triphenylphosphine oxide content % Triphenylphosphine oxide content by normalisation by Gc analysis After crystallisation: 0%

EXAMPLE 2

Example 1 was repeated but using (S)-1-(1,2,4-triazolo[1,5a]-pyrimid-7-yl)ethanol (4.2 g) as starting material. After ethyl acetatelt-butyl methyl ether trituration, a crude product (10.9 g) was isolated which was triturated with propan-2-ol (10 ml) at <5° C. for 2 hours; a solid (4.8 g) was isolated by filtration, crystallised from propan-2-ol (total volume 8 ml) and the crystals washed with propan-2-ol (2×1 ml) to give crystals (4.5 g) and residue (0.4 g) which were analysed for triphenylphosphine oxide content.

The crystals and residue were recombined and recrystallised from propan-2-ol (25 ml) to give residue (2.6 g) and (R)-7-[1-(4-chlorophenoxy)ethyl]-1,2,4-triazolo[1,5a]pyrimidine (2.4 g), 35%, optical rotation $[\alpha]_D=143°$ (c=1.05, methanol) which was analysed for triphenylphosphine oxide content.

% Triphenylphosphine oxide content by normalisation by Gc analysis

After 1st crystallisation: 0%

After recrystallisation: 0%

EXAMPLE 3

A solution of dilsopropyl azodicarboxylate (6.17 g) in dry tetrahydrofuran (10 ml) was added dropwise to a stirred mixture of 1-(1,2,4-triazolo[1,5a]pyrimidin-7-yl)ethanol (5 g, 30 mmol), 4-chlorophenol (3.92 g), triphenyiphosphine (8 g) and ethyl acetate (70 ml) under nitrogen at 0–5° C. and stirred overnight at ambient temperature. Magnesium chloride (5.8 g, 2 eq) was added and the stirred mixture heated under reflux for 2 hours. t-Butyl methyl ether (50 ml) was added and the mixture cooled to 0° C., filtered and the filter pad washed with a 6:4 mixture of ethyl acetate and t-butyl methyl ether (100 ml. The filtrate was washed with water (2×100 ml), sodium hydroxide solution (1M, 4×25 ml), brine (30 ml), dried ($MgSO_4$) and the solvent evaporated to give a solid (13.6 g) which was analysed for triphenylphosphine oxide content.

The solid was recrystallised from propan-2-ol (35 ml) with seeding to yield 7-[1-(4-chlorophenoxy)ethyl-1,2,4-triazolo]-1,5a]pyrimidine (3.4 g), 43%, which was analysed for triphenylphosphine oxide content.

% Triphenylphosphine oxide content by normalisation by Gc analysis

After complexation: 5.7%

After crystallisation: 0.49%

EXAMPLE 4

A solution of diisopropyl azodicarboxylate (11 g, 1.1 eq) in toluene (20 ml) was added dropwise to a stirred mixture of 1-(1,2,4-triazolo[1,5-a]pyrimidin-7-yl)ethanol (8.1 g, recrystallised from tetrahydrofuran, 49 mmol), 4-chlorophenol (6.35 g, 1 eg), triphenylphosphine (12.95 g, 1 eq) and toluene (200 ml) under nitrogen at 0–5° C. and the mixture then stirred at ambient temperature overnight. Magnesium chloride (9.5 g, -~2 eq) was added and the stirred mixture heated under reflux for 1.5 hours, cooled to −5° C. and filtered, washing the filter pad with further toluene (2×50 ml). ml). The combined filtrate was washed with water (2×200 ml), sodium hydroxide solution (1M, 2×50 ml), and then water (2×50 ml) and then the solvent evaporated. Propan-2-ol (50 ml) was added to the residue and the solvent evaporated; this was repeated. The residue was dissolved in propan-2-ol (50 ml), seeded with a crystal of product, and left to stand at 0–5° C. for 72 hours. The product was collected by filtration, washed with cold propan-2-ol (2×20 ml) and dried in vacuo to yield 7-[1-(4-chlorophenoxy)ethyl]1,2,4-triazolo[1,5-a]pyrimidine (7.1 g, 53%), which was analysed for triphenylphosphine oxide content.

% Triphenylphosphine oxide content by normalisation by Gc analysis

After crystallisation: 0.4%

EXAMPLE 5

A solution of diisopropyl azodicarboxylate (4.47 g, 1.05 eq) in tetrahydrofuran (10ml) was added dropwise to a stirred mixture of 1-(1,2,4-triazolo[1,5-a]pyrimidin-7-yl)ethanol (3.45 g), triphenylphosphine (5.52 g) and 5'-chloro-2'-hydroxyacetanilide (3.9 g) in tetrahydrofuran (100 ml) at 0–5° C. under nitrogen and the mixture then stirred at ambient temperature overnight. Water (0.3 ml) was added and the stirred mixture heated under reflux for 15 minutes. Magnesium chloride (5 g; 2.5 eq) was added and the stirred mixture heated under reflux for 2 hours, then cooled to 0° C. and filtered, washing the filter pad with tetrahydrofuran (25 ml). The solvent was evaporated, and the residue was dissolved in water (100 ml) and ethyl acetate (200 ml). The organic layer was washed with water (100 ml), sodium hydroxide (1M, 2×50 ml) and brine (50 ml), then dried ($MgSO_4$) and the solvent evaporated. The residue was dissolved in warm propan-2-ol (45 ml) and allowed to crystallise at 5° C. overnight; the crystals formed were washed with propan-2-ol (2×10 ml) and dried in vacuo to yield 5'chloro-2'-[1-(1,2,4triazolo[1,5a]pyrimidin-7-yl)ethoxy]acetanilide (4.66 g), 67% which was analysed for triphenylphosphine oxide content.

% Triphenylphosphine oxide content by nmr analysis

After crystallisation: 0%

EXAMPLE 6

A solution of diisopropyl azodicarboxylate (12.18 g, 1.1 eq) in toluene (42 ml) was added dropwise to a stirred mixture of 1-(1,2,4-triazolo[1,5-a]pyrimidin-7-yl)ethanol (8.9 g), triphenylphosphine (14.33 g) and 4-chloro-2-nitrophenol (9.5 g, 1 eg) in toluene (140 ml) at 0–5° C. under nitrogen and the mixture stirred for 1 hour, warmed to ambient temperature and then left to stand overnight. The solvent was evaporated, and the residue dissolved in tetrahydrofuran (200 ml). Magnesium chloride (11 g; 2 eq) was added and the stirred mixture heated under reflux for 1.5 hours, cooled to ambient temperature and filtered. The filtrate solvent was evaporated and the residue partitioned between ethyl acetate (400 ml) and water (200 ml). The organic layer was washed with water (200 ml), then sodium hydroxide (1M, 100 ml) and brine (100 ml), dried ($MgSO_4$) and the solvent evaporated. The residue was triturated with boiling propan-2-ol (200 ml), cooled and filtered to give 7-[1-(4chloro-2-nitrophenoxy)ethyl]-1,2,4-triazolo[1,5-a]pyrimidine, (10 g), 57%, mp 158° C. which was analysed for triphenylphosphine oxide content.

% Triphenylphosphine oxide content by nmr analysis

After propan-2-ol trituration: 0%

EXAMPLE 7

The solvent was evaporated from a mixture of (R)-7-[1-(4-chlorophenoxy)ethyl]-1,2,4-triazolo[1,5-a]pyrimidne (1 g) and triphenylphosphine oxide (1 g) in ethanol (25 ml), then samples were taken and evaporated, and the residues were analysed by nmr, Gc, HPLC. The mixture was redissolved in ethanol (25 ml), and magnesium chloride (0.7 g, ~2 eq) added. The mixture was stirred for 1 hour then the solvent evaporated to give an oil; this was redissolved in ethanol (25 ml,) and the solvent evaporated; ethyl acetate (20 ml) was added to the residue, then the solvent was evaporated to give a solid. The solid was then extracted with a 2:1 mixture of ethyl acetate and petroleum ether (b.p. 40–60° C.) (2×15 ml) and the mixture filtered. Evaporation of the filtrate solvent yielded (R)-7-[1-(4-chlorophenoxy) ethyl]-1,2,4-triazolo[1,5-a]pyrimidine (0.55 g) as a solid. The filter pad was then washed with ethyl acetate (2×10 ml) and the solvent evaporated to yield further product (0.11 g). The product was analysed for triphenylphosphine oxide content.

% Triphenylphosphine oxide content by normalisation by Gc analysis

Before complexation: 61.2%

After complexation: 2.1%

EXAMPLE 8 - PRODUCTION SCALE

A reactor was loaded with 4chlorophenol (2.89 kg), (S)-1-(1,2,4-triazolo[1,5-a]pyrimidin-7-yl)ethanol (3.69 kg), triphenylphosphine (5.9 kg) and tetrahydrofuran (69I). The suspension was cooled to 5–10° C. and diisopropyl azodicarboxylate (4.79 kg) was added over 2 hours. After complete addition of diisopropyl azodicarboxylate the solution was stirred while warming to ambient temperature. Magnesium chloride (anhydrous; 4.3 kg; ~2 eq) was added and the reaction mixture was heated under reflux for 1 hour. Cooling to 10° C. yielded a suspension which was collected by filtration. The filter pad was washed with tetrahydrofuran (10 I). The mother liquor was refilled into the reactor and tetrahydrofuran replaced with toluene by distillation of inert diluent (100 I) and addition of toluene (100 I) at the same rate. When the inert diluent exchange was complete the solution was cooled to ambient temperature and extracted twice with water. The organic phase was separated, filtered, then charged to the reaction vessel. Toluene (64 I) was distilled off, propan-2ol (128 I) added, and the solvent mixture (123 I) was then distilled off. After this solvent exchange the reaction mixture was slowly cooled to ambient temperature for crystallization of the product. The product was filtered off and washed with propan-2-ol (10 I). (R)-7-[1-(4-chlorophenoxy)ethyl]-1,2,4-triazolo[1,5-a]pyrimidine, (2.29 kg) was isolated after drying in vacuo at 40° C. HPLC-analysis: 99.92%; chiral HPLC: ee=100%. No triphenylphosphine oxide was detectable by HPLC analysis.

EXAMPLE 9

A solution of diisopropyl azodicarboxylate (6.18 g, 1.1 eq) in dry tetrahydrofuran (11 ml) was added dropwise at 0–5° C. over 1 hour to a stirred mixture of 1-(1,2,4-triazolo[1,5-a]pyrmidin-7-yl)ethanol (5.008 g), 4-chlorophenol (3.929 g, 1.1 eg), triphenylphosphine (8.021 g, 1.1 eq) and dry tetrahydrofuran (61 ml) under nitrogen, and then stirred overnight at ambient temperature. A sample of the mixture was evaporated and the residue was analysed by Gc for triphenylphosphine oxide content.

A sample (27 ml) of the mixture was taken. Magnesium chloride (1.9 g, 2 eq) was added at ambient temperature and stirred overnight. The mixture was cooled to 0° C. for one hour then filtered, and the filter pad washed with tetrahydrofuran (10 ml). The solvent was removed from the filtrate in vacuo. The residue was dissolved in toluene (20 ml) and the resulting solution filtered. The filtrate was washed with water (20 ml) and the organic layer was separated. The organic solvent was removed in vacuo to yield a residue (4.23 g) which was analysed for triphenylphosphine oxide content.

Ice cold propan-2-ol (5 ml) was added to the residue, and the resulting mixture was left at 0° C. overnight. The mixture was then filtered, and the filter pad washed with ice cold propan-2-ol (2 ml), to yield 7-[1-(4-chlorophenoxy)ethyl]-1,2,4-triazolo[1,5-a]pyrimidine (0.81 g; 29%) which was analysed for triphenylphosphine oxide content.

% Triphenylphosphine oxide content by normalisation by Gc analysis.

Before complexation: 50.5%

After complexation: 17.1%

After propan-2-ol trituration: 0%

EXAMPLE 10

A sample (27 ml) of the mixture from the reaction described in example 9 was taken, and magnesium chloride (1.9 g, 2 eq) was added. The mixture was heated under reflux for 30 minutes, then cooled to 0° C. for one hour and filtered, and the filter pad washed with tetrahydrofuran (10 ml). The solvent was removed from the filtrate in vacuo. The residue was extracted with toluene (20 ml) and the resulting mixture filtered. The filtrate was washed with water (20 ml) and the organic layer was separated. The organic solvent was removed in vacuo to yield a residue (3.25 g) which was analysed for triphenylphosphine oxide content.

Ice cold propan-2-ol (5 EQ was added to the residue, and the resulting mixture was left at 0° C. overnight. The mixture was then filtered, and the filter pad washed with ice cold propan-2-ol (2 ml), to yield 7-[1-(4chlorophenoxy)ethyl]1,2,4-triazolo[1,5a]pyrimidine pyrimidine (1.12 g; 39%) which was analysed for triphenylphosphine oxide content.

% Triphenylphosphine oxide content by normalisation Gc analysis.

Before complexation: 50.5%

After complexation: 7.0%

After propan-2-ol trituration: 0%

EXAMPLE 11

A sample (27 ml) of the mixture from the reaction described in example 9 was taken, and magnesium chloride (0.475 g, 0.5 eq) was added. The mixture was heated under reflux for 2.5 hours. The mixture was cooled to 0° C. for one hour and then filtered, and the filter pad washed with tetrahydrofuran (10 ml). The solvent was removed from the filtrate in vacuo. The residue was dissolved in toluene (20 ml) ml) and the resulting solution filtered. The filtrate was washed with water (20 ml) and the organic layer was separated. The organic solvent was removed in vacuo to yield a residue (4.77 g) which was analysed for triphenylphosphine oxide content.

Ice cold propan-2ol (5 ml was added to the residue, and the resulting mixture was left at 0° C. overnight. The mixture was then filtered, and the filter pad washed with ice cold propan-2-ol (2 ml), to yield 7-[1-(4-chlorophenoxy)ethyl]-1,2,4-triazolo[1,5a]pyrimidine (0.91 g; 32%) which was analysed for triphenylphosphine oxide content.

% Triphenylphosphine oxide content by normalisation Gc analysis.

Before complexation: 50.5%

After complexation: 28.1%

After propan-2-ol trituration: 0%

EXAMPLE 12

A solution of diIsopropyl azodicarboxylate (1.23 g) in dichloromethane (2 ml) was added dropwise over one hour to a mixture of 1-(1,2,4-triazolo[1,5a]pyrimidin-7-yl) ethanol (1.01 g), 4-chlorophenol (0.78 g), triphenylphosphine (1.61 g) and dichloromethane (12 ml) under nitrogen at 0–5° C. and then stirred overnight at ambient temperature. Magnesium chloride (1.14 g, 2 eq) was added and the mixture heated under reflux for two hours, cooled to 0° C. for 30 minutes and filtered, washing the filter pad with dichloromethane. The solvent was removed in vacuo, and the residue dissolved in toluene (20 ml). The mixture was filtered, water (20 ml) was added and then the organic layer was separated. The solvent was removed in vacuo to yield a solid (2.40 g) which was analysed for triphenylphosphine oxide content.

Propan-2-ol (5 ml) was added to the solid and the mixture allowed to stand at 0–5° C. for 3 days. The mixture was filtered and the solid washed with cold (0° C.) propan-2ol (2 ml) to give 7-[1-(4chlorophenoxy)ethyl]-1,2,4-triazolo[1,5-a]pyrimidine (0.361 g; 22%) which was analysed for triphenylphosphine oxide content.

% Triphenylphosphine oxide content by normalisation by Gc analysis

Before complexation: 50.5%

After complexation: 22.7%

After propan-2-ol trituration: 0.1%

EXAMPLE 13

A solution of diisopropyl azodicarboxylate (6.17 g) in dry tetrahydrofuran (7 ml) was added slowly dropwise to a stirred mixture of 1-(1,2,4-trazolol[1,5-a]pyrimidin-7-yl) ethanol (5 g), 4-chlorophenol (3.92 g) and triphenylphosphine (8.02 g) in dry tetrahydrofuran (60 ml) under nitrogen at 5–10° C. The mixture was stirred for 30 minutes at 5–10° C. under nitrogen, then the mixture was allowed to warm to ambient temperature. The mixture was then stirred at ambient temperature for one hour. The solvent was removed in vacuo to yield a residue (23.4 g) which was analysed for triphenylphosphine oxide content.

A sample (2.01 g) of the residue was taken, and zinc chloride (0.38 g, 1.1 eq) and ethanol (30 ml) were added. The mixture was heated under reflux for 30 minutes, then cooled to ambient temperature, filtered and the filter pad washed with ethanol (10 ml). The solvent was removed from the filtrate in vacuo. Toluene (20 ml) was added to the residue, and the mixture was filtered. Water (20 ml) was added and the organic layer separated. The solvent was removed in vacuo to yield the residue (1.53 g) which was analysed for triphenylphosphine oxide content.

Propan-2-ol (5 ml) was added to the residue and the mixture allowed to stand at 0–5° C. for 3 days. The mixture was filtered and the solid collected was washed with cold (0° C.) propan-2-ol (2 ml) to give 7-[1-(4chlorophenoxy)ethyl]-1,2,4triazolo[1,5-a]pyrimidine (0.132 g; 25%) which was analysed for triphenylphosphine oxide content.

% Triphenylphosphine oxide content by normalisation by Gc analysis

Before complexation: 49.4%

After complexation: 14.6%

After propan-2ol trituration: 0%

EXAMPLE 14

A sample (2.00 g) of the residue from the Mitsunobu reaction described in example 13 was taken, and manganese (II) chloride tetrahydrate (0.55 g, 1.1 eq) and tetrahydrofuran (30 ml) were added. The mixture was heated under reflux for 2 hours, cooled to ambient temperature, filtered and the filter pad washed with tetrahydrofuran (10 ml). The solvent was removed from the filtrate in vacuo. Toluene (20 ml) was added and the mixture was filtered. Water (20 ml) was added to the filtrate. The organic layer was separated and the solvent removed in vacuo to yield a residue (0.80 g) which was analysed by Gc for triphenylphosphine oxide content.

% Triphenylphosphine oxide content by normalisation by Gc analysis

Before complexation: 49.4%

After complexation: 28.4%

EXAMPLE 15

A sample (2.00 g) of the residue from the Mitsunobu reaction described in example 13 was taken, and magnesium chloride mono(ethyl acetate) (0.95 g, 2 eq) and ethyl acetate (20 ml) were added. The mixture was heated under reflux for 2 hours, then cooled to ambient temperature, filtered and the filter pad washed with ethyl acetate (10 ml). Water (20 ml) was added and the organic layer separated. The solvent was removed in vacuo to yield a residue (2.54 g) which was analysed by Gc for triphenylphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4chlorophenoxy)ethyl]-1,2,4-triazolo[1,5-a]pyrimidine (0.234 g; 33%) which was analysed for triphenylphosphine oxide content.

% Triphenylphosphine oxide content by normalisation by Gc analysis

Before complexation: 49.4%

After complexation: 14.9%

After propan-2-ol trituration: 0.6%

EXAMPLE 16

A sample (2.00 g) of the residue from the Mitsunobu reaction described in example 13 was taken, and propan-2-ol (5 ml) was added. The mixture was allowed to stand at 0–5° C. for 1.5 hours. The mixture was filtered and solid washed with cold (0° C.) propan-2-ol (2 ml) to yield a solid which was analysed by Gc for triphenylphosphine oxide content.

Magnesium chloride (0.55 g, 2.2 eq) and tetrahydrofuran (30 ml) were added and the mixture heated under reflux for 2 hours. The mixture was cooled to 0° C. for one hour, filtered and the filter pad washed with tetrahydrofuran (10 ml). The solvent was removed in vacuo. Toluene (20 ml) was added and the mixture was filtered. Water (20 ml) was added to the filtrate, and organic layer was separated. The solvent was removed in vacuo to yield a solid (0.56 g) which was analysed by Gc for triphenylphosphine oxide content.

% Triphenylphosphine oxide content by normalisation by Gc analysis

Before trituration: 49.4%

After propan-2do trituration: 65.0%

After complexation: 7.7%

EXAMPLE 17

A sample (2.00 g) of the residue from the Mitsunobu reaction described in example 13 was taken, and tetrahydrofuran (30 ml) and a solution of magnesium chloride (0.55 g, 2 eq) in methanol (10 ml) were added to the mixture. The mixture was stirred for 2.5 hours at ambient temperature. The solvent was removed in vacuo, toluene (70 ml) was added and the mixture was filtered. The solvent was removed in vacuo to yield a solid (1.11 g) which was analysed by Gc for triphenylphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4-chlorophenoxy)ethyl]1,2,4-triazolo[1,5-a]pyrimidine (0.036 g; 5%) which was analysed for triphenylphosphine oxide content.

% Triphenylphosphine oxide content by normalisation by Gc analysis

Before complexation: 49.4%

After complexation: 25.1%

After propan-2-ol trituration: 0.2%

EXAMPLE 18

A sample (2.00 g) of the residue from the Mitsunobu reaction described in example 13 was taken, and zinc iodide (0.89 g, 1.1 eq) and ethanol (30 ml) were added. The mixture was heated under reflux for 2 hours, then cooled to 0° C. for one hour. The mixture was filtered and the filter pad washed with ethanol (10 ml). The solvent was removed in vacuo, toluene (20 ml) was added to the residue and the mixture was filtered. Water (20 ml) was added and the organic layer was separated. The solvent was removed in vacuo to yield a solid (1.37 g) which was analysed by Gc for triphenylphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4-chlorophenoxy)ethyl]-1,2,4-triazolol[1,5-a]pyrimidine (0.291 g) which was analysed for triphenylphosphine oxide content.

% Triphenylphosphine oxide content by normalisation by Gc analysis

Before complexation: 49.4%

After complexation: 41.8%

After propan-2-ol trituration: 15.1%

EXAMPLE 19

A sample (2.00 g) of the residue from the Mitsunobu reaction described in example 13 was taken, and copper (I) chloride (0.28 g, 1.1 eq) and tetrahydrofuran (30 ml) were added. The mixture was heated under reflux for 2 hours, then cooled to 0° C. for one hour, filtered and the filter pad washed with tetrahydrofuran (10 ml). The solvent was removed in vacuo, toluene (20 ml) was added and the mixture was filtered. Water (20 ml) was added and the organic layer was separated and dried over magnesium sulphate. The organic solvent was removed in vacuo to yield a solid (1.38 g) which was analysed by Gc for triphenylphosphine oxide content.

Propan-2-ol (5 ml) was added to the solid and the mixture allowed to stand at 0–5° C. for three days. The mixture was filtered and the solid washed with cold (0° C.) propan-2-ol (2 ml) to give 7-[1 -(4chlorophenoxy)ethyl]-1,2,4triazolo[1,5-a]pyrimidine (0.442 g; 63%) which was analysed for triphenylphosphine oxide content.

% Triphenylphosphine oxide content by normalisation by Gc analysis

Before complexation: 49.4%

After complexation: 43.6%

After propan-2-ol trituration: 0.2%

EXAMPLE 20

A sample (2.00 g) of the residue from the Mitsunobu reaction described in example 13 was taken, and iron (III) chloride (0.45 g, 1.1 eq) and tetrahydrofuran (30 ml) were added. The mixture was heated under reflux for 2 hours, cooled to 0° C. for one hour, filtered and the filter pad washed with tetrahydrofuran (10 ml). Toluene (20 ml) was added to the filtrate and the mixture was filtered. Water (20 ml) was added to the filtrate and organic layer was separated. The organic layer was dried over magnesium sulphate, and the solvent removed in vacuo to yield a solid (1.08 g) which was analysed by Gc for triphenylphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4-chlorophenoxy)ethyl]-1,2,4-triazolo[1,5-a]pyrimidine (0.186 g; 27%) which was analysed for triphenylphosphine oxide content.

% Triphenylphosphine oxide content by normalisation by Gc analysis

Before complexation: 49.4%

After complexation: 36.5%

After propan-2-ol trituration: 0.8%

EXAMPLE 21

Diethyl azodicarboxylate (1.06 g) in tetrahydrofuran (2 ml) was added dropwise over 1 hour to a mixture of 1-(1,2,4-triazolo[1,5-a]pyrimidin-7-yl)ethanol (1.00 g), 4-chlorophenol (0.78 g), triphenylphosphine (1.62 g) and tetrahydrofuran (12 ml) which was stirred under nitrogen at 0–5° C. The mixture was allowed to stand overnight at ambient temperature. Magnesium chloride (1.14 g, 2 eq) was added, and the mixture was heated under reflux for 2 hours then cooled to 0° C. for one hour. The mixture was littered and the filter pad washed with tetrahydrofuran (10 ml). The solvent was removed from the filtrate in vacuo. Toluene (20 ml) was added and the mature was filtered. Water (20 ml) was added to the filtrate and the organic layer was separated. The solvent was removed in vacuo to yield a solid (1.16 g) which was analysed by Gc for triphenyiphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4-chlorophenoxy)ethyl]-1,2,4-triazolo[1,5a]pyrimidine (0.61 g; 36%) which was analysed for triphenylphosphine oxide content.

% Triphenylphosphine oxide content by normalisation by Gc analysis

Before complexation: 50.5%

After complexation: 9.5%

After propan-2-ol trituration: 0.2%

EXAMPLE 22

A sample (2.00 g) of the residue from the Mitsunobu reaction described in example 13 was taken, and tetrahydrofuran (30 ml) and magnesium chloride hexahydrate (1.04 g, 2 eq) were added. The mixture was heated under reflux for 2 hours, then cooled to 0° C. for one hour and filtered, and the filter pad washed with tetrahydrofuran (10 ml). The solvent was removed in vacuo, toluene (20 ml) was added and the mixture was filtered. Water (20 ml) was added to the filtrate and the organic layer was separated. The solvent was removed in vacuo to yield a solid (0.95 g) which was analysed by Gc for triphenylphosphine oxide content.

Propan-2-ol (5 ml) was added to the solid and the mixture allowed to stand at 0–5° C. for 3 days. The mixture was filtered and the solid washed with cold (0° C.) propan-2-ol (2 ml) to give 7-[1-(4chlorophenoxy)ethyl]-1,2,4-triazolo[1,5a]pyrimidine (0.153 g; 22%) which was analysed for triphenylphosphine oxide content.

% Triphenylphosphine oxide content by normalisation by Gc analysis

Before complexation: 49.4%

After complexation: 27.4%

After propan-2-ol trituration: 0.35%:

EXAMPLE 23

A sample (2.00 g) of the residue from the Mitsunobu reaction described in example 13 was taken, and tetrahydrofuran (30 ml) and samarium (III) chloride (1.31 g, 2 eg) were added. The mixture was heated under reflux for 2 hours, then cooled to 0° C. for 2 hours, filtered and the filter pad washed with tetrahydrofuran (10 ml). The solvent was removed in vacuo, toluene (20 ml) added and the mixture was filtered. Water (20 ml) was added and the organic layer was separated. The solvent was removed in vacuo to yield a solid (0.1 g) which was analysed for triphenylphosphine oxide content.

% Triphenylphosphine oxide content by normnalisation by Gc analysis

Before complexation: 49.4%

After complexation: 2.0%

EXAMPLE 24

A solution of diisopropyl azodicarboxylate (1.23 g) in tetrahydrofuran (2 ml) was added over 10 minutes to a stirred mixture of 4-chlorophenol (0.78 g), triphenylphosphine (1.62 g) and tetrahydrofuran (12 ml) under nitrogen at 0–5° C. Magnesium chloride (1.14 g, 2 eq) and 1-(1,2,4-triazolo[1,5-a]pyrimidin-7-yl)ethanol (1.00 g) were added and the mixture was stirred under nitrogen at ambient temperature overnight The mixture was heated under reflux for 2 hours, then allowed to cool to 0° C. for one hour, filtered and the filter pad washed with tetrahydrofuran (10 ml). The solvent was removed in vacuo. Toluene (20 ml) was added to the residue and the mixture was filtered. Water (20 ml) was added and the organic layer was separated. The solvent was removed in vacuo to yield a solid (2.06 g) which was analysed by Gc for triphenylphosphine oxide content.

% Triphenylphosphine oxide content by normalisation by Gc analysis

After complexation: 34.7%

EXAMPLE 25 - LAB SCALE SYNTHESIS WHICH IS SCALABLE TO PRODUCTION SCALE

The reactor was loaded with 4-chlorophenol (58.5 g), (S)1-(1,2,4-triazolo[1,5-a]pyrimidin-7-yl)ethanol (50 g), triphenylphosphine (85 g) and toluene (900 ml). The suspension was cooled to 5–10° C. and diisopropyl azodicarboxylate (65 ml) was added over 2 hours. After complete addition of diisopropyl azodicarboxylate the solution was stirred while warming to ambient temperature. The reaction mixture was re-cooled to 0° C. and filtered. The filtrate, magnesium chloride (anhydrous; 31.1 g) and celite (25.5 g) were combined in the reactor. Toluene (500 ml) was distilled off and the remaining mixture was cooled to 0° C. The suspension formed was removed by filtration. Further magnesium chloride (2.6 g) and celite (2.5 g) were added to the filtrate. Toluene (200 ml) was removed by distillation. The residue was cooled to 0° C. and filtered. The filtercake was washed with toluene. The reactor was loaded with the filtrate, and toluene was removed by azeotropic distillation with propan-2-ol. The product crystallised from propan-2-ol at 40° C. while cooling to 20° C. The product was collected by filtration and washed with propan-2-ol. After drying, the product (R)-7-[1-(4-chlorophenoxy)ethyl]-1,2,4-triazolo[1,5-a]pyrimidine (61.1 g) was obtained (yield: 73.6%; HPLC analysis: 99.1%; chiral HPLC: ee=100%). No triphenylphosphine oxide was detectable by HPLC analysis.

Comparative Example 1

This experiment was conducted to compare the effect of trituration with propan-2-ol on a mixture, comprising desired product, triphenylphosphine oxide and dihydro-diisopropyl azodicarboxylate, which either has or has not been subjected to the addition of a metal salt.

A mixture of 7-[1-(4-chlorophenoxy)ethyl]-1,2,4-triazolo[1,5-a]pyrimidine (0.274), triphenylphosphine oxide (0.19 g) and dihydro-diisopropyl azodicarboxylate (0.32 g) [29%, 28% and 17.2% by normalisation by Gc analysis respectively] was triturated with propan-2-ol (2 ml) and cooled to 0° C. for three hours. The mixture was filtered, and the filter pad washed with ice cold propan-2-ol (2 ml), to yield 7-[1-(4-chlorophenoxy)ethyl]-1,2,4triazolo[1,5-a]pyrimidine (0.269 g) which was analysed for triphenylphosphine oxide content.

% Triphenylphosphine oxide content by normalisation by Gc analysis

Before propan-2-ol trituration: 28%

After propan-2-ol trituration: 9.1%

Although the percentage of triphenylphosphine oxide in the sample has been reduced by the trituration process, there is still 9.1% present. This can be compared with the result seen in example 11, where the percentage triphenylphosphine oxide after complexation with magnesium chloride was 28.1% which reduced to 0% after trituration with propan-2-ol. It is thus apparent that greater triphenylphosphine oxide removal can be achieved in a mixture which has been subjected to the addition of a metal salt than in one which has not.

Comparative Example 2

A series of ten laboratory scale reactions in which diethyl azodicarboxylate was added at 3–6° C. to a mixture of triphenylphosphine, 4-chlorophenol, and (S)-1-(1,2,4-triazolol[1,5-a]pyrimidin-7-yl)ethanol in tetrahydrofuran was carried out. The mixtures were stirred at ambient temperature for 3–4 hours, then the product obtained by standard work-up procedures.

The standard work-up procedures comprised removing the solvent and dissolving the residue in diethyl ether, washing with aqueous sodium hydroxide, water, and saturated brine, drying over magnesium sulphate and removing the solvent; triturating the residue with diethyl ether and removing the solid; passing the filtrate through a silica gel pad using diethyl ether as eluant; combining the relevant fractions and removing the solvent to yield a residue which was analysed by HPLC; combining samples still containing triphenylphosphine oxide and further purifying by recrystallisations, passing through silica gel pads using diethyl ether as eluant, and/or hot filtering with propan-2-ol. A sample of (R-7-[1-(4chlorophenoxy)ethyl]-1,2,4-triazolo[1,5-a]pyrimidine (165.5 g), in which no triphenylphosphine oxide was detectable, was obtained.

It is evident from the above details that many manipulations were required before the triphenylphosphine oxide could be adequately removed to yield pure product. Such elaborate procedures are not suitable for scaling up to industrial scale syntheses. This can be compared with example 8 where an industrial scale synthesis is described in which the addition of magnesium chloride after the main reaction is complete reduces the number of manipulations required to obtain pure product. A similar comparison may be made with example 25. These comparisons illustrate the advantage of the present invention.

What is claimed is:

1. A process for the preparation of compounds of formula I

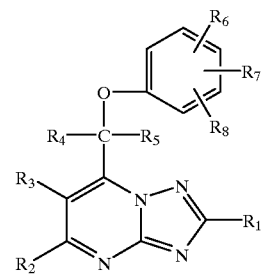

including pharmaceutically acceptable salts, racemates, enantiomers, diastereoisomers and mixtures thereof in which:

$R_1$ represents H or one of the following groups: $C_{1-6}$alkyl, $C_{1-6}$alkoxy or $C_{1-6}$alkanoyl wherein each of the foregoing groups is optionally substituted by one or more of halo or cyano,; $R_2$ and $R_3$ independently represent H or one of the following groups: $C_{1-6}$alkyl, $C_{1-6}$alkoxy or $C_{1-6}$alkanoyl, $C_{1-6}$alkylthio, $C_{1-6}$alkylsulphinyl or $C_{1-6}$alkylsulphony wherein each of the foregoing groups is optionally substituted by one or more of halo or cyano;

$R_4$ and $R_5$ independently represent H, $C_{1-6}$ralkyl or $R_4$ and $R_5$ combined together with the carbon atom to which they are attached represent $C_{3-6}$cycloalkylidene wherein each alkyl or cycloalkylidene is optionally substituted with one or more of halo, cyano or $C_{1-6}$alkyl; and $R_6$, $R_6$, and $R_8$ independently represent H, halo, nitro, cyano or one of the following groups: $C_{1-6}$alkyl, $C_{1-6}$alkanoyl, $C_{1-6}$alkoxy, $C_{2-6}$alkoxycarbony, carboxy, $C_{1-6}$alkanoyloxy, $C_{1-6}$alkylthio, $C_{1-6}$alkylsulphinyl, $C_{2-6}$alkylsulphonyl, $C_{1-6}$alkylsulphonylamino, sulphamoyl, carbamoyl, $C_{2-6}$alkylcarbamoyl or $C_{1-6}$alkanoylamino wherein each of the foregoing groups is optionally substituted by one or more halo or cyano,; and any nitrogen atom is optionally substituted with one or more $C_{1-6}$alkyl; sulphonylamino, sulphamoyl, carbamoyl, $C_{2-6}$alkylcarbamoyl or $C_{1-6}$alkanoylamino;

said process comprising the reaction involving an alcohol of formula II

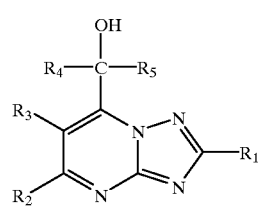

in which $R_1$, $R_2$, $R_3$, $R_4$ and $R_5$ are as defined above, with a phenol of formula III

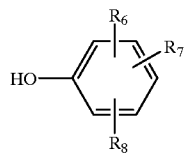

III in which R₆, R₇ and R₈ are as defined above, in the presence of an inert diluent and at least one redox couple comprising an oxidizing agent and a reducing agent which is selected from a tri-substituted phosphine, arsine or stibine wherein the reducing agent becomes oxidized; wherein
   a) a metal salt is added to form a complex or complexes with the oxidized reducing agent or agents produced in the process, and
   b) the resultant complex or complexes is/are separated from the desired product.

2. A process as claimed in claim 1 in which the metal salt of step a) is added after the reaction involving the compounds of formulae II and III.

3. A process as claimed in claim 2 in which the metal salt of step a) is added subsequent to a diluent change after the reaction involving the compounds of formulae II and III.

4. A process as claimed in claim 1 in which the metal salt is added in a quantity ranging from 0.25 to 5 molar equivalents of the reducing agent.

5. A process as claimed in claim 1 in which the metal salt is magnesium chloride, copper (I) chloride, or zinc chloride.

6. A process as claimed in claim 1 in which the metal salt is magnesium chloride.

7. A process as claimed in claim 1 in which the separation step b) further comprises purification of the compound of formula I by trituration with a suitable solvent and/or crystallisation from a suitable solvent.

8. A process as claimed in claim 1 for the preparation of 7-[1-(4-chlorophenoxy)ethyl]-1,2,4-triazolo[1,5-a]pyrimidine including the racemate, enantiomers and mixtures thereof, said process comprising the reaction involving the compound of formula II which is 1-(1,2,4-triazolo[1,5-a]pyrimidin-7-yl)ethanol, including the racemate, enantiomers and mixtures thereof, and the compound of formula III which is 4-chlorophenol in the presence of an inert diluent and at least one redox couple comprising an oxidising agent, which is diisopropyl azodicarboxylate or diethyl azodicarboxylate, and a reducing agent, which is triphenylphosphine, wherein the reducing agent becomes oxidised; wherein
   a) a halide salt of magnesium, copper (I), iron (III), samarium (III) or zinc is added after the reaction involving the compounds of formulae II and III to form a complex or complexes with the oxidised reducing agent produced in the process, and
   b) the resultant complex or complexes is/are separated from the desired product by filtration, and optionally further purification of the desired product is carried out by trituration with propan-2-ol and/or crystallisation from propan-2-ol.

9. A process as claimed in claim 1 in which the compound of formula II is (S)-1-(1,2,4-triazolo[1,5-a]pyrimidin-7-yl)ethanol, the compound of formula III is 4-chlorophenol and the compound of formula I is (R)-7-[1-(4-chlorophenoxy)ethyl]-1,2,4-triazolo[1,5-a]pyrimidine.

10. A process as claimed in claim 9 in which the reducing agent is triphenylphosphine.

11. A process as claimed in claim 9 or 10 in which the oxidising agent is diisopropyl azodicarboxylate.

12. A process as claimed in claim 9, 10 or 11 in which the metal salt is magnesium chloride.

13. A process as claimed in claim 1 in which the level of tri-substituted phosphine, is reduced to 15% of the product mixture or less.

14. A process as claimed in claim 12 in which the compound of formula I is further purified by trituration with propan-2-ol and/or crystallisation from propan-2-ol.

15. A process as claimed in claim 1 or 8 in which the mixture is heated under reflux at the boiling point temperature of the inert diluent after step a) and before step b), for up to six hours.

16. A process as claimed in claim 1 in which the level of tri-substituted phosphines, arsine or stibine is reduced to 15% of the product mixture or less.

17. A process as claimed in claim 1 in which the compound of formula I is further purified by trituration with propan-2-ol and/or crystallization from propan-2-ol.

18. A process as claimed in claim 1 in which the mixture is heated under reflux at the boiling point temperature of the inert diluent after step a) and before step b), for up to six hours.

* * * * *

UNITED STATES PATENT AND TRADEMARK OFFICE
CERTIFICATE OF CORRECTION

PATENT NO. : 6,225,469 B1
DATED : May 1, 2001
INVENTOR(S) : Holman et al.

It is certified that error appears in the above-identified patent and that said Letters Patent is hereby corrected as shown below:

Column 18,
Line 31, "$C_{1-6}$ralkyl" should be -- $C_{1-6}$alkyl --.
Line 43, "$C_{2-6}$alkylsulphonyl" should be -- $C_{1-6}$alkylsulphonyl --.

Column 19,
Line 33, "claim 1" should be -- claim 5 --.

Column 20,
Line 22, delete "or 10".
Line 24, delete ", 10 or 11".
Lines 26-35, remove claims 13-15 printed in the patent as they are duplicates of claims 16-18.

Signed and Sealed this

Ninth Day of July, 2002

*Attest:*

JAMES E. ROGAN
*Attesting Officer*     Director of the United States Patent and Trademark Office